United States Patent
Lee

(10) Patent No.: US 10,501,790 B2
(45) Date of Patent: Dec. 10, 2019

(54) PCR AMPLIFICATION METHODS FOR DETECTING AND QUANTIFYING SULFATE-REDUCING BACTERIA IN OILFIELD FLUIDS

(71) Applicant: Baker Hughes, a GE company, LLC, Houston, TX (US)

(72) Inventor: Crystal Lee, Houston, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 0 days.

(21) Appl. No.: 15/899,227

(22) Filed: Feb. 19, 2018

(65) Prior Publication Data

US 2018/0291428 A1 Oct. 11, 2018

Related U.S. Application Data

(63) Continuation-in-part of application No. 15/066,421, filed on Mar. 10, 2016, now abandoned.

(60) Provisional application No. 62/132,195, filed on Mar. 12, 2015.

(51) Int. Cl.

| | |
|---|---|
| C12Q 1/68 | (2018.01) |
| C09K 8/532 | (2006.01) |
| C09K 8/02 | (2006.01) |
| C10G 31/00 | (2006.01) |
| C09K 8/58 | (2006.01) |
| C09K 8/62 | (2006.01) |
| C12Q 1/686 | (2018.01) |

(52) U.S. Cl.
CPC ............... *C12Q 1/686* (2013.01); *C09K 8/02* (2013.01); *C09K 8/58* (2013.01); *C09K 8/62* (2013.01); *C10G 31/00* (2013.01)

(58) Field of Classification Search
None
See application file for complete search history.

(56) References Cited

U.S. PATENT DOCUMENTS

| | | | | |
|---|---|---|---|---|
| 5,016,714 A * | 5/1991 | McCabe | ............. | C09K 8/605 166/308.1 |
| 6,531,281 B1 * | 3/2003 | Magot | ............. | C12Q 1/689 435/6.18 |
| 2004/0091882 A1 * | 5/2004 | Magot | ............. | C12Q 1/689 435/6.18 |

FOREIGN PATENT DOCUMENTS

| | | |
|---|---|---|
| CN | 101089195 | 12/2007 |
| CN | 103088133 A | 5/2013 |
| WO | 2004048607 A1 | 6/2004 |
| WO | 2007068926 A2 | 6/2007 |
| WO | 2014058721 | 4/2014 |

OTHER PUBLICATIONS

Gadberry MD, Malcomber ST, Doust AN, Kellogg EA. Primaclade—a flexible tool to find conserved PCR primers across multiple species. Bioinformatics. Apr. 1, 2005; 21(7):1263-4. Epub Nov. 11, 2004. (Year: 2004).*

Sharma N, Bambusch L, Le T, Morey A, Hayman M, Montez SJ. InstantLabs® Salmonella species detection method: matrix extension. J AOAC Int. Nov.-Dec. 2014; 97(6):1585-91. (Year: 2014).*

Genbank Accession No. EF442947—Desulfobacca acetoxidans DSM 11109 AprB (aprB) and AprA (aprA)(submitted by Meyer et al. Feb 2007, retrieved on Sep. 28, 2018 from http://www.ncbi.nlm.nih.gov/nuccore/EF442947). (Year: 2007).*

Genbank Accession No. EF442948—Desulfomonile tiedjei DSM 6799 AprB (aprB) and AprA (aprA) genes (submitted by Meyer et al. Feb 2007, retrieved on Sep. 28, 2018 from http://www.ncbi.nlm.nih.gov/nuccore/EF442948). (Year: 2007).*

Plaskon NE, Adelman ZN, Myles KM. Accurate strand-specific quantification of viral RNA. PLoS One. Oct. 22, 2009; 4(10):e7468 pp. 1-8. (Year: 2009).*

Dhillon, Ashita et al., "Molecular Characterization of Sulfate-Reducing Bacteria in the Guaymas Basin," Applied & Environmental Microbiology, pp. 2765-2772 (May 2003).

Int'l Search Report & Written Opinion in PCT/US2016/022071, dated Jun. 16, 2016.

Ben-Dov E, Brenner A, Kushmaro A., "Quantification of sulfate-reducing bacteria in industrial wastewater, by real-time polymerase chain reaction (PCR) using dsrA and apsA genes," Microb Ecol. Oct. 2007; 54(3):439-51, Epub Mar. 10, 2007.

Wei L, Ma F, Zhao G., "Composition and dynamics of sulfate-reducing bacteria during the waterflooding process in the oil field application," Bioresour Technol. Apr. 2010, 101 (8):2643-50, Epub Dec. 14, 2009.

* cited by examiner

Primary Examiner — Gary Benzion
Assistant Examiner — Olayinka A Oyeyemi
(74) Attorney, Agent, or Firm — Mossman, Kumar & Tyler, P.C.

(57) ABSTRACT

At least one nucleic acid from a sulfate-reducing bacteria (SRB) may be extracted from an oilfield fluid and may be amplified by a PCR amplification method in the presence of at least one primer to form an amplification product. The primer(s) may be or include a sequence including, but not necessarily limited to, SEQ ID NO: 20, SEQ ID NO: 21, and mixtures thereof. The amplification product may be hybridized with a probe specific for a fragment of an alpha subunit of an APS gene, and a presence of hybridization and a degree of hybridization may be detected.

15 Claims, 3 Drawing Sheets
Specification includes a Sequence Listing.

SRB Assay
Forward Primer Name 1: aprb1.5_Fwd primer (SEQ ID NO:1)
Forward Primer Sequence 1 (5' – 3'): CCNGTNCGYACCGGTAAATGG

FIG. 1

SRB Assay
Forward Primer Name 2: aprb2b4_Fwd primer (SEQ ID NO:2)
Forward Primer Sequence 2 (5' – 3'): CCNGTNGGCGCNTGGTTC

FIG. 2

SRB Assay
Forward Primer Name 3: aprb3 Fwd (SEQ ID NO:3)
Forward Primer Sequence 3 (5' – 3'): GAGAACTTGTGNCCGGA

FIG. 3

SRB Assay
Forward Primer Name 4: dsr_ Fwd primer (SEQ ID NO:4)
Forward Primer Sequence 4 (5' – 3'): CAYACCCAGGGYTGG

FIG. 4

SRB Assay
Forward Primer Name 5: dsr_ Fwd primer (SEQ ID NO:5)
Forward Primer Sequence 5 (5' – 3'): CACACBCAAGGDTGG

FIG. 5

SRB Assay
Forward Primer Name 6: dsr_ Fwd primer (SEQ ID NO:6)
Forward Primer Sequence 6 (5' – 3'): CAYACBCAAGGCTGG

FIG. 6

SRB Assay
Forward Primer Name 7: dsr_ Fwd primer (SEQ ID NO:7)
Forward Primer Sequence 7 (5' – 3'): CATACDCAGGGHTGG

FIG. 7

SRB Assay
Forward Primer Name 8: dsr_ Fwd primer (SEQ ID NO:8)
Forward Primer Sequence 8 (5' – 3'): CACACDCAGGGRTGG

FIG. 8

SRB Assay
Forward Primer Name 9: dsr_ Fwd primer (SEQ ID NO:9)
Forward Primer Sequence 9 (5' – 3'): CACACDCAGGGYTGG

FIG. 9

SRB Assay
Forward Primer Name 10: dsr_ Fwd primer (SEQ ID NO:10)
Forward Primer Sequence 10 (5' – 3'): CATACCCAGGGNTAY

FIG. 10

SRB Assay
Forward Primer Name 11: dsr_Fwd primer (SEQ ID NO:11)
Forward Primer Sequence 11 (5' – 3'): CATACWCAGGGHTAT

FIG. 11

SRB Assay
Reverse Primer Name 1: aprb1.5 _Rev primer (SEQ ID NO:12)
Reverse Primer Sequence 1 (5' – 3'): CCATACNGGRTACCAKGCRCG

FIG. 12

SRB Assay
Reverse Primer Name 2: aprb2b4 _Rev primer (SEQ ID NO:13)
Reverse Primer Sequence 2 (5' – 3'): GGAAGTCTTCCCANGCTTC

FIG. 13

SRB Assay
Reverse Primer Name 3: aprb3 Rev primer (SEQ ID NO:14)
Reverse Primer Sequence 3 (5' – 3'): TGGGAAGABTTCCTVGACATG

FIG. 14

SRB Assay
Reverse Primer Name 4: dsr_Rev primer (SEQ ID NO:15)
Reverse Sequence 4 (5' – 3'): GTGTARCAGTTRCCRCA

FIG. 15

SRB Assay
Probe Name 1: aprb1.5_probe (SEQ ID NO:16)
Probe Sequence 1 (5' – 3'): CAGATCATGATCAAYGGTGARTCYTA

FIG. 16

SRB Assay
Probe Name 2: aprb2b4_probe (SEQ ID NO:17)
Probe Sequence 2 (5' – 3'): CGAAGACTACTGNGNVACC

FIG. 17

SRB Assay
Probe Name 3: aprb3_probe (SEQ ID NO:18)
Probe Sequence 3 (5' – 3'): CGCCCACDCCGTCNGCVCAGG

FIG. 18

SRB Assay
Probe Name 4: dsr_probe (SEQ ID NO:19)
Probe Sequence 4 (5' – 3'): TSAACATGTGCGGCG

FIG. 19

SRB Assay
(SEQ ID NO:20)
Primer Sequence (5' – 3'): AATAAATCATAAGAGAACTTGTGNCCGGA

FIG. 20

SRB Assay
(SEQ ID NO:21)
Primer Sequence (5' – 3'): AATAAATCATAATGGGAAGABTTCCTVGACATG

FIG. 21

PCR AMPLIFICATION METHODS FOR DETECTING AND QUANTIFYING SULFATE-REDUCING BACTERIA IN OILFIELD FLUIDS

CROSS-REFERENCE TO RELATED APPLICATIONS

This application is a continuation-in-part application of U.S. patent application Ser. No. 15/066,421 filed Mar. 10, 2016, now abandoned, which in turn claims the benefit of U.S. Provisional Patent Application Ser. No. 62/132,195 filed Mar. 12, 2015, both of which are incorporated herein by reference in their entireties.

TECHNICAL FIELD

The present invention relates to amplifying, optionally detecting and optionally quantifying sulfate-reducing bacteria (SRB), and more specifically relates to rapid amplification of SRB using real-time quantitative polymerase chain reactions (qPCR).

BACKGROUND

The presence of SRB in many environments is undesirable, particularly in concentrations sufficient to cause significant corrosion of metals with aqueous solutions, including fresh and seawaters, having the SRB therein. SRBs are present in a variety of environments, including oil- and gas-bearing formations, soils, and wastewater. SRBs are also present in the gut of ruminant animals, particularly domestic animals (e.g. cattle) used as protein sources for human consumption.

Sulfate-reducing bacteria, such as members of the genera *Desulfovibrio* and *Desulfotomaculum*, may reduce sulfate and/or sulfite under suitable conditions (e.g. anaerobic conditions) and generate hydrogen sulfide, an odiferous, and poisonous gas. In addition, the SRB may contact metals thereby causing corrosion to the metal, such as metal structures and conduits. "Sulfate-reducing bacteria" is defined herein to be bacteria capable of reducing sulfate to sulfite and/or bacteria capable of reducing sulfite to sulfide, regardless of the taxonomic group of the bacteria.

Traditionally, the monitoring of microbial populations has employed microbial growth tests where a sample is diluted to various levels and used to inoculate microbial growth media designed to favor the growth of various types of bacteria. After days to several weeks of incubation, the growth tests are scored based on the presence or absence of growth in these various microbiological media. Unfortunately, as numerous researchers show, only about 0.1% to about 10% bacteria from environmental samples can actually grow in an artificial medium, and a significant portion of bacteria growing in the media are not actually the target bacteria. Therefore, growth tests are unable to provide the accurate quantification of target bacteria in the samples. In addition, obtaining results from a serial dilution assay may take as long as three to four weeks.

To circumvent problems associated with such growth-based methods, many culture-independent genetic techniques have been developed in the past decade to detect pathogens in the field of medicine, the food industries, the oil and gas industries, and the like. Because many ecosystems have a relatively low abundance of microorganisms, the polymerase chain reaction (PCR) has been widely used to amplify the genetic signals of microbes in complex environmental samples. However, traditional PCR-based methods are significantly biased by amplification efficiency and the depletion of PCR reagents.

Real-time quantitative PCR (qPCR) may be used to detect and quantify a number of microorganisms. Quantitative PCR has also been used to determine the abundance of microorganisms in many different types of complex environmental samples, such as sediments, water, wastewater, and marine samples. qPCR may provide more accurate and reproducible quantification of microorganisms because qPCR quantifies the PCR products during the logarithmic phase of the reactions, which does not occur during traditional PCR methods. Moreover, qPCR offers a dynamic detection range of six orders of magnitude or more, does not need post-PCR manipulation, and has the capability of high throughput analysis.

Digital PCR (dPCR) may be used to directly quantify and clonally amplify nucleic acids including DNA, cDNA, and/or RNA. dPCR may be more precise method than PCR and/or qPCR. Traditional PCR carries out one reaction per single sample. dPCR may carry out a single reaction within a sample, but the sample may be separated into a large number of partitions, and the reaction may be individually carried out within each partition. The separation may allow for a more reliable collection and a more sensitive measurement of nucleic acid amounts within the sample. dPCR may be useful for studying variations in gene sequences, such as copy number variants, point mutations, and the like, and dPCR may be routinely used for clonal amplification of samples for "next-generation sequencing."

It would be desirable to have a method of detecting and optionally quantifying SRB within a sample that is cost-effective and may occur in real time.

SUMMARY

There is provided, in one form, a method of decreasing SRB in oilfield fluids by altering an amount of a microbial agent within the oilfield fluid to form an altered oilfield fluid based on an amount of at least one SRB within an oilfield fluid where the altered oilfield fluid may have a decreased amount of SRB as compared to the oilfield fluid. The amount of the SRB may be determined by amplifying at least one nucleic acid of the SRB in the presence of at least one primer to form an amplification product. The amplification product may be hybridized with a probe specific for a fragment of an alpha subunit of an APS gene. The presence of hybridization and a degree of hybridization may be detected where the presence of hybridization indicates the presence of the SRB, and where the degree of hybridization enumerates the SRB. The nucleic acid(s) may be extracted from the oilfield fluid prior to amplifying the nucleic acid(s). The primer(s) may have or include a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO.20, SEQ ID NO:21, and mixtures thereof.

An alternative non-limiting embodiment of the method may also include an oilfield fluid, such as but not limited to an oilfield water, a production fluid, a fracturing fluid, a drilling fluid, a completion fluid, a workover fluid, a packer fluid, a gas fluid, a crude oil, and mixtures thereof.

In another non-limiting embodiment, a method of determining an amount of SRB within an oilfield fluid may include amplifying at least one nucleic acid of at least one SRB in the presence of at least one primer to form an amplification product. The amplifying may occur by a PCR amplification method, and the nucleic acid(s) may be extracted from the oilfield fluid prior to amplifying the nucleic acid(s). The primer(s) may include a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO.20, SEQ ID NO:21, and mixtures thereof. The method may further include hybridizing the amplification product with a probe specific for a fragment of an alpha subunit of an APS gene, and detecting a presence of hybridization and a degree of hybridization. The presence of hybridization may indicate the presence of the SRB. The degree of hybridization may enumerate the SRB to determine an amount of SRB in the oilfield fluid.

In another non-limiting embodiment, a PCR amplification method is provided. The method may include amplifying at least one nucleic acid of at least one SRB in the presence of at least one primer to form an amplification product. SRB's DNA may be extracted from an oilfield fluid prior to amplifying the nucleic acid(s). The primer(s) may include a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO.20, SEQ ID NO:21, and mixtures thereof.

BRIEF DESCRIPTION OF THE DRAWINGS

In order to more fully understand the drawings referred to in the detailed description, a brief description of each drawing is presented here:

FIGS. 1-15 and 20-21 (SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO.20, SEQ ID NO:21) represent the nucleotide sequences of a primer usable to detect SRB; and FIGS. 16, 17, 18, and 19 (SEQ ID NO:16, SEQ ID NO:17, SEQ ID NO:18, and SEQ ID NO: 19) represent the nucleotide sequence of a probe usable to detect SRB.

DETAILED DESCRIPTION

It has been discovered that an amount of antimicrobial agent may be added to an oilfield fluid to form an altered oilfield fluid based on an amount of at least one SRB within an oilfield fluid. Alternatively, the amount of the antimicrobial agent, e.g. biocide, present may be altered within the altered oilfield fluid based on an amount of at least one SRB within the oilfield fluid. Non-limiting examples of microbial agents are those additives typically used to decrease the amount of SRB within an oilfield fluid. 'Decreasing' the amount of SRB may occur by killing the bacteria and/or by inactivating the bacteria from producing sulfur compounds, such as but not limited to sulfates, sulfites, mercaptans, and the like.

A polymerase chain reaction (PCR) amplification method may be used to amplify at least one nucleic acid of at least one SRB in the presence of at least one primer to form an amplification product. This method of amplification, optional detection and optional quantification of SRBs present in a particular sample is much quicker than previous methods of detecting SRBs. For example, the PCR amplification methods described below may occur in an amount of time less than about 7 calendar days, alternatively less than 2 calendar days, or less than 24 hours in another non-limiting embodiment. In yet another non-limiting embodiment, the PCR amplification methods may occur in less than 8 hours.

In an alternative embodiment, the method of amplification, optional detection and optional quantification may occur in an amount of time less than about a 7 calendar days, alternatively less than 2 calendar days, or less than 24 hours in another non-limiting embodiment. In yet another non-limiting embodiment, the PCR amplification, optional detection and optional quantification methods may occur in less than 8 hours.

'Amplification' as defined herein refers to any in vitro method for increasing the number of copies of a nucleotide sequence with the use of a DNA polymerase, such as a PCR method of amplification in a non-limiting embodiment. PCR amplification methods may include from about 10 cycles independently to about 50 cycles of denaturization and synthesis of a DNA molecule.

Prior to amplifying the nucleic acid(s) of the SRBs, the nucleic acids must first be extracted from a sample. The sample may be in any form necessary to obtain the SRB, such as a fluid sample containing the SRB, a ground-up version of a field sample where it would be beneficial to determine whether the SRB are present in the tissue, and the like. In an alternative embodiment, a surface and/or surface solids suspected of having SRB contamination may be swabbed, and the swab may be placed in a fluid to obtain the SRB fluid sample. Non-limiting examples of a sample may be a food product, an animal tissue, a human tissue, a water sample, a lab surface, a metal surface, a paper mill industry surface, a wastewater within a wastewater treatment facility, a sample from the paint industry, and combinations thereof.

The nucleic acid may be or include, DNA, RNA (e.g. mRNA), and combinations thereof. The nucleic acid(s) from the SRB within the sample may be extracted from the sample prior to amplifying the nucleic acid(s). Such extraction techniques of the nucleic acids from the sample may be carried out by standard techniques, which are well known to persons skilled in the art.

A non-limiting example of an extraction technique may be or include using the QIAamp Tissue Kit (QIAGEN, Hilden, Germany), the MP Bio Soil DNA kit, and the like. DNA from the SRBs may be extracted from a sample using the QIAamp Tissue Kit as is well known in the art.

Once the nucleic acid(s) are extracted, the nucleic acid(s) may be combined with at least one primer in a reaction well to start and/or improve the amplification of the nucleic acids using a PCR method. The primer(s) may be or include a sequence including, but not necessarily limited to, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO.20 and SEQ ID NO:21 (FIGS. 1-2), and mixtures thereof. The primer(s) may be specific for amplification of at least a fragment of an alpha subunit of an APS reductase gene. Alternatively, the primer(s) may include an oligonucleotide from the alpha subunit of the APS reductase gene.

APS reductase (also known as Adenylylsulfate Reductase) allows the reduction of adenosine phosphosulfate (APS—a product of the activation of sulfate by ATP sulfurylase). APS reductase is a cytoplasmic enzyme containing two subunits (alpha and beta) known to be involved only in the anaerobic respiration of sulfate. This enzyme may not be present in non-sulfate-reducing organisms, since it is not involved in the assimilatory reduction that allows the incorporation of sulfur into various molecules necessary for life, such as amino acids and vitamins. Therefore, detecting fragments of the gene(s) that may code for APS reductase may allow for the detection of a SRB.

'Primer' as defined herein refers to a single-stranded oligonucleotide that is extended by covalent bonding of nucleotide monomers during amplification or polymerization of a nucleic acid molecule. 'Oligonucleotide' as defined herein refers to a synthetic or natural molecule comprising a covalently linked sequence of nucleotides that are joined by a phosphodiester bond between the 3' position of the pentose of one nucleotide and the 5' position of the pentose of the adjacent nucleotide.

The components for a PCR method of amplification must be added to a reaction well prior to performing the PCR method of amplification. In a non-limiting embodiment, the components may include the forward primer (also known as a sense primer), the reverse primer (also known as an antisense primer), PCR buffer, dNTP, DNA, water, and combinations thereof. The amounts of the components within a reaction well are very well known to those skilled in the art, and the components within the reaction well may vary depending on the amounts of the other components present.

dNTPs are deoxynucleotide triphosphates included in a solution for purposes of PCR amplification. Stock dNTP solutions may have a pH of about 7, and the stability of dNTPs during repeated cycles of PCR may leave about 50% of the dNTPs remaining after about 50 PCR cycles. The concentration of each of the four dNTPs in solution ranges from about 20 µM to about 200 µM.

PCR methods of amplification require specific conditions of temperature and reaction time. In one non-limiting embodiment there may be present additional agents and/or reagents which may be useful for the fragment of the gene for the alpha subunit of APS reductase, to which the primers (mentioned previously) have hybridized, to be copied identically. Such conditions are well known to those skilled in the art. An average PCR program runs about 30 to about 65 cycles, but more or less cycles may be used depending on the conditions of the DNA, desired number of amplification products, time constraints, etc.

Computer processing may be used to analyze the crude amplification products. The PCR program mentioned above is strictly a non-limiting example and should not be deemed to limit the invention here.

In another non-restrictive version of the PCR amplification method, an internal amplification control can be helpful to prevent an ambiguous interpretation of results. In a non-limiting instance, an absence of amplification by PCR may be due to a difficulty including, but not necessarily limited to, to problems of inhibition of the reaction, or to the absence of a target, that is, the absence of DNA from the SRB.

In another non-limiting embodiment, the amplification of one or more fragments of the APS reductase gene can permit the detection of the fragment of the APS reductase gene, including, but not necessarily limited to the gene for the alpha subunit of the APS reductase. Optionally, gene amplification products can be subjected to hybridization with a probe specific for a fragment of the gene for the alpha subunit of the APS reductase where the probe may be labeled in a detectable way, including but not necessarily limited to fluorescent labeling, radioactive labeling, chemiluminescent labeling, enzymatic labeling, and combinations thereof. 'Gene' is defined herein to mean a DNA sequence containing information required for expression of a polypeptide or protein.

Hybridizing the amplification product with a probe also requires particular conditions of temperature, reaction time, and preventing the hybridization of the oligonucleotide with sequences other than the gene for the alpha subunit of APS reductase. In a non-limiting example, the hybridization temperature may range from about 55° C. to about 65° C. The reaction time for the hybridization may range from about 0 seconds independently to about 60 seconds. As used herein with respect to a range, "independently" means that any threshold may be used together with another threshold to give a suitable alternative range.

The probe is a fragment of DNA used to detect the presence of nucleotide sequences that are complementary to the sequence in the probe. The probe hybridizes to a single-stranded nucleic acid, whose base sequence allows probe-target base pairing due to complementarity between the probe and the target (e.g. single-stranded DNA from the SRB). First, the probe may be denatured (by heating or under alkaline conditions, such as exposure to sodium hydroxide) into single stranded DNA (ssDNA) and then hybridized to the target ssDNA. The hybridization may occur when the target ssDNA and probe are immobilized on a membrane (e.g. a gel) or in situ. 'Target' as used herein refers to DNA of the SRB.

A presence of hybridization and a degree of hybridization may be detected. The presence of hybridization may indicate the presence of the SRB, and the degree of hybridization may enumerate the SRB.

In a non-limiting embodiment, the method may be performed by
amplifying at least one nucleic acid of at least one SRB in the presence of at least one primer to form an amplification product where the nucleic acid(s) are extracted from a sample prior to amplifying the nucleic acid(s). The primer(s) may include an oligonucleotide having a nucleotide sequence including, but not necessarily limited to, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO.20, SEQ ID NO:21, and mixtures thereof;
optionally hybridizing the amplification product with a probe having a nucleotide sequence; and
optionally detecting the hybridization complex formed between the product of amplification and the probe to indicate the presence of SRB in the sample.

The type of sulfur-species bacteria that may be detected by the methods may be or include, but are not limited to, *Desulfovibrio vulgaris, Desulfovibrio desulfuricans, Desulfovibrio aespoeensis, Thermodesulfobium narugense, Desulfotomaculum carboxydivorans, Desulfotomaculum ruminis, Desulfovibrio africanus, Desulfovibrio hydrothermalis, Desulfovibrio piezophilus, Desulfobacterium corrodens,*

Sulfate-reducing bacterium QLNR1, *Desulfobacterium catecholicum, Desulfobulbus marinus, Desulfobulbus, Desulfobulbus propionicus, Desulfocapsa thiozymogenes, Desulfocapsa sulfexigens, Desulforhopalus vacuolatus, Desulforhopalus, Desulfofustis glycolicus* strain, *Desulforhopalus singaporensis, Desulfobacterium, Desulfobacterium zeppelinii* strain, *Desulfobacterium autotrophicum, Desulfobacula phenolica, Desulfobacula toluolica* Tol2, Sulfate-reducing bacterium JHA1, *Desulfospira joergensenii, Desulfobacter, Desulfobacter postgatei, Desulfotignum, Desulfotignum balticum, Desulforegula conservatrix, Desulfocella, Desulfobotulus sapovorans, Desulfofrigus, Desulfonema magnum, Desulfonema limicola, Desulfobacterium indolicum, Desulfosarcina variabilis, Desulfatibacillum, Desulfococcus multivorans, Desulfococcus, Desulfonema ishimotonii, Desulfococcus oleovorans* Hxd3, *Desulfococcus niacini, Desulfotomaculum, Desulfotomaculum nigrificans, Desulfotomaculum halophilum, Desulfotomaculum acetoxidans, Desulfotomaculum gibsoniae, Desulfotomaculum sapomandens* strain, *Desulfotomaculum thermosapovorans, Desulfotomaculum geothermicum, Desulfosporosinus meridiei, Delta proteobacterium, Thermodesulforhabdus norvegica, Desulfacinum infernum, Desulfacinum hydrothermale, Desulforhabdus amnigena, Desulforhabdus, Desulfomonile tiedjei, Desulfarculus baarsii, Desulfobacterium anilini, Desulfovibrio profundus* strain, *Desulfomicrobium baculatum, Desulfocaldus hobo, Desulfovibrio, Desulfovibrio piger, Desulfovibrio ferrophilus, Desulfonatronovibrio hydrogenovorans, Desulfovibrio acrylicus, Desulfovibrio salexigens, Desulfovibrio oxyclinae, Desulfonauticus submarinus, Desulfothermus naphthae, Thermodesulfobacterium, Thermodesulfobacterium hveragerdense, Thermodesulfobacterium thermophilum, Thermodesulfatator indicus, Thermodesulfovibrio yellowstonii, Desulfosporosinus orientis, Desulfotomaculum thermobenzoicum, Desulfotomaculum solfataricum, Desulfotomaculum luciae* strain, *Desulfobacca acetoxidans, Desulfovibrio alaskensis, Desulfovibrio magneticus, Desulfosporosinus acidiphilus, Desulfotomaculum kuznetsovii, Desulfovibrio sulfodismutans, Desulfonatronum lacustre, Desulfohalobium retbaense, Desulfonauticus autotrophicus, Thermodesulfobacterium commune, Thermodesulfovibrio islandicus, Thermodesulfovibrio, Desulfotomaculum thermoacetoxidans, Desulfotomaculum thermocisternum, Desulfotomaculum australicum, Desulfotomaculum reducens*, and combinations thereof.

In the foregoing specification, the invention has been described with reference to specific embodiments thereof, and has been described as effective in providing methods and compositions for PCR amplification methods, and primers and/or probes useful therefor. However, it will be evident that various modifications and changes can be made thereto without departing from the broader spirit or scope of the invention as set forth in the appended claims. Accordingly, the specification is to be regarded in an illustrative rather than a restrictive sense. For example, specific samples, nucleic acids, forward primers, reverse primers, probes, PCR cycles, SRB, internal controls (plasmids), and the like falling within the claimed parameters, but not specifically identified or tried in a particular composition or method, are expected to be within the scope of this invention.

The present invention may suitably comprise, consist or consist essentially of the elements disclosed and may be practiced in the absence of an element not disclosed. For instance, the PCR amplification method may consist of or consist essentially of amplifying at least one nucleic acid of at least one SRB in the presence of at least one primer to form an amplification product; wherein the at least one SRB is extracted from an oilfield fluid or a solid prior to amplifying the at least one nucleic acid; the nucleic acid(s) is extracted from a sample prior to amplifying the nucleic acid(s); the primer(s) may include a nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO.20, SEQ ID NO:21, and mixtures thereof. Oilfield fluids are defined herein to include, but not necessarily be limited to, crude oil and other fluids produced from subterranean formations, including produced waters, oilfield waters, production fluids, fracturing fluids, drilling fluids, completion fluids, workover fluids, packer fluids, gas fluids, and refinery fluids including processed crude oil, refined products, process and waste water, midstream fluids, downstream fluids, and the like.

The method of determining an amount of SRB within an oilfield fluid may consist of or consist essentially of amplifying at least one nucleic acid of at least one SRB in the presence of at least one primer to form an amplification product; wherein the amplifying occurs by a PCR amplification method wherein the at least one nucleic acid is extracted from the oilfield fluid prior to amplifying the at least one nucleic acid; wherein the at least one primer comprises a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO.20, SEQ ID NO:21, and mixtures thereof; hybridizing the amplification product with a probe specific for a fragment of an alpha subunit of an APS gene; and detecting a presence of hybridization and a degree of hybridization; wherein the presence of hybridization indicates the presence of the at least one SRB; and wherein the degree of hybridization enumerates the at least one SRB; and determining an amount of SRB in the oilfield fluid.

The method of decreasing SRB in oilfield fluids may consist of or consist essentially of adding an amount of a antimicrobial agent to an oilfield fluid having an amount of at least one SRB within an oilfield fluid; wherein the amount of the at least one SRB is determined by amplifying at least one nucleic acid of the at least one SRB in the presence of at least one primer to form an amplification product; hybridizing the amplification product with a probe specific for a fragment of an alpha subunit of an APS gene; detecting a presence of hybridization and a degree of hybridization; and decreasing the amount of SRB by killing and/or deactivating the bacteria where the altered oilfield fluid comprises a decreased amount of SRB as compared to the oilfield fluid.

As used herein, the terms "comprising," "including," "containing," "characterized by," and grammatical equivalents thereof are inclusive or open-ended terms that do not exclude additional, unrecited elements or method acts, but also include the more restrictive terms "consisting of" and "consisting essentially of" and grammatical equivalents thereof. As used herein, the term "may" with respect to a material, structure, feature or method act indicates that such is contemplated for use in implementation of an embodiment of the disclosure and such term is used in preference to the more restrictive term "is" so as to avoid any implication that other, compatible materials, structures, features and methods usable in combination therewith should or must be, excluded.

As used herein, the singular forms "a," "an," and "the" are intended to include the plural forms as well, unless the context clearly indicates otherwise.

As used herein, the term "and/or" includes any and all combinations of one or more of the associated listed items.

As used herein, relational terms, such as "first," "second," "top," "bottom," "upper," "lower," "over," "under," etc., are used for clarity and convenience in understanding the disclosure and accompanying drawings and do not connote or depend on any specific preference, orientation, or order, except where the context clearly indicates otherwise.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" in reference to a given parameter is inclusive of the stated value and has the meaning dictated by the context (e.g., it includes the degree of error associated with measurement of the given parameter).

What is claimed is:

1. A method of decreasing sulfate-reducing bacteria (SRB) in oilfield fluids comprising:
   altering an amount of a microbial agent within an oilfield fluid to form an altered oilfield fluid based on an amount of at least one SRB within an oilfield fluid; wherein the amount of the at least one SRB is determined by:
      amplifying at least one nucleic acid of the at least one SRB in the presence of at least one primer to form an amplification product; wherein the at least one nucleic acid is extracted from the oilfield fluid prior to amplifying the at least one nucleic acid; wherein the at least one primer comprises a sequence selected from the group consisting of SEQ ID NO.20, SEQ ID NO:21, and mixtures thereof;
      hybridizing the amplification product with a probe specific for a fragment of an alpha subunit of an Adenylylsulfate Reductase gene; and
      detecting a presence of hybridization and a degree of hybridization, wherein the presence of hybridization indicates the presence of the at least one SRB, and wherein the degree of hybridization enumerates the at least one SRB; and
   decreasing the amount of SRB by killing and/or deactivating the SRB wherein the altered oilfield fluid comprises a decreased amount of SRB as compared to the oilfield fluid.

2. The method of claim 1, wherein the oilfield fluid is selected from the group consisting of produced waters, oilfield waters, production fluids, fracturing fluids, drilling fluids, completion fluids, workover fluids, packer fluids, gas fluids, crude oils, refinery fluids, processed crude oils, refined products, process and waste waters, midstream fluids, downstream fluids, and mixtures thereof.

3. The method of claim 1, wherein the probe is detectably labeled.

4. The method of claim 1, wherein the at least one sulfate-reducing bacteria is selected from the group consisting of *Desulfovibrio vulgaris*, *Desulfovibrio desulfuricans*, *Desulfovibrio aespoeensis*, *Thermodesulfobium narugense*, *Desulfotomaculum carboxydivorans*, *Desulfotomaculum ruminis*, *Desulfovibrio africanus*, *Desulfovibrio hydrothermalis*, *Desulfovibrio piezophilus*, *Desulfobacterium corrodens*, Sulfate-reducing bacterium QLNR1, *Desulfobacterium catecholicum*, *Desulfobulbus marinus*, *Desulfobulbus*, *Desulfobulbus propionicus*, *Desulfocapsa thiozymogenes*, *Desulfocapsa sulfexigens*, *Desulforhopalus vacuolatus*, *Desulforhopalus*, *Desulfofustis glycolicus* strain, *Desulforhopalus singaporensis*, *Desulfobacterium*, *Desulfobacterium zeppelinii* strain, *Desulfobacterium autotrophicum*, *Desulfobacula phenolica*, *Desulfobacula toluolica* Tol2, Sulfate-reducing bacterium JHA1, *Desulfospira joergensenii*, *Desulfobacter*, *Desulfobacter postgatei*, *Desulfotignum*, *Desulfotignum balticum*, *Desulforegula conservatrix*, *Desulfocella*, *Desulfobotulus sapovorans*, *Desulfofrigus*, *Desulfonema magnum*, *Desulfonema limicola*, *Desulfobacterium indolicum*, *Desulfosarcina variabilis*, *Desulfatibacillum*, *Desulfococcus multivorans*, *Desulfococcus*, *Desulfonema ishimotonii Desulfococcus oleovorans* Hxd3, *Desulfococcus niacini*, *Desulfotomaculum*, *Desulfotomaculum nigrificans*, *Desulfotomaculum halophilum*, *Desulfotomaculum acetoxidans*, *Desulfotomaculum gibsoniae*, *Desulfotomaculum sapomandens* strain, *Desulfotomaculum thermosapovorans*, *Desulfotomaculum geothermicum*, *Desulfosporosinus meridiei*, Delta proteobacterium, *Thermodesulforhabdus norvegica*, *Desulfacinum infernum*, *Desulfacinum hydrothermale*, *Desulforhabdus amnigena*, *Desulforhabdus*, *Desulfomonile tiedjei*, *Desulfarculus baarsii*, *Desulfobacterium anilini*, *Desulfovibrio profundus* strain, *Desulfomicrobium baculatum*, *Desulfocaldus hobo*, *Desulfovibrio*, *Desulfovibrio piger*, *Desulfovibrio ferrophilus*, *Desulfonatronovibrio hydrogenovorans*, *Desulfovibrio acrylicus*, *Desulfovibrio salexigens*, *Desulfovibrio oxyclinae*, *Desulfonauticus submarinus*, *Desulfothermus naphthae*, *Thermodesulfobacterium*, *Thermodesulfobacterium hveragerdense*, *Thermodesulfobacterium thermophilum*, *Thermodesulfatator indicus*, *Thermodesulfovibrio yellowstonii*, *Desulfosporosinus orientis*, *Desulfotomaculum thermobenzoicum*, *Desulfotomaculum* solfataricum, *Desulfotomaculum luciae* strain, *Desulfobacca acetoxidans*, *Desulfovibrio alaskensis*, *Desulfovibrio magneticus*, *Desulfosporosinus acidiphilus*, *Desulfotomaculum kuznetsovii*, *Desulfovibrio sulfodismutans*, *Desulfonatronum lacustre*, *Desulfohalobium retbaense*, *Desulfonauticus autotrophicus*, *Thermodesulfobacterium commune*, *Thermodesulfovibrio islandicus*, *Thermodesulfovibrio*, *Desulfotomaculum thermoacetoxidans*, *Desulfotomaculum thermocisternum*, *Desulfotomaculum australicum*, *Desulfotomaculum reducens*, and combinations thereof.

5. The method of claim 1, further comprising circulating the altered oilfield fluid within a subterranean reservoir wellbore, wherein the altered oilfield fluid is selected from the group consisting of altered fracturing fluids, altered drilling fluids, altered completion fluids, altered workover fluids, altered packer fluids, altered produced waters, altered oilfield waters, altered production fluids, altered gas fluids, altered crude oils, altered refinery fluids, altered processed crude oils, altered refined products, altered process and waste waters, altered midstream fluids, altered downstream fluids, and combinations thereof.

6. A method of decreasing sulfate-reducing bacteria (SRB) in oilfield fluids comprising:
   altering an amount of a microbial agent within an oilfield fluid based on an amount of at least one SRB within the oilfield fluid to form an altered oilfield fluid; wherein the oilfield fluid is selected from the group consisting of oilfield water, a production fluid, a fracturing fluid, a drilling fluid, a completion fluid, a workover fluid, a packer fluid, a gas fluid, a crude oil, and mixtures thereof; wherein the amount of the at least one SRB is determined by:

amplifying at least one nucleic acid of the at least one SRB in the presence of at least one primer to form an amplification product; wherein the at least one nucleic acid is extracted from the oilfield fluid prior to amplifying the at least one nucleic acid; wherein the at least one primer comprises a sequence selected from the group consisting of SEQ ID NO.20, SEQ ID NO:21, and mixtures thereof;

hybridizing the amplification product with a probe specific for a fragment of an alpha subunit of an Adenylylsulfate Reductase gene; and detecting a presence of hybridization and a degree of hybridization;
wherein the presence of hybridization indicates the presence of the at least one SRB; and wherein the degree of hybridization enumerates the at least one SRB; and decreasing the amount of SRB by killing and/or deactivating the SRB.

7. The method of claim 6, further comprising circulating the altered oilfield fluid within a subterranean reservoir wellbore wherein the altered oilfield fluid is selected from the group consisting of an altered fracturing fluid, an altered drilling fluid, an altered completion fluid, an altered workover fluid, an altered packer fluid, and combinations thereof.

8. A method of determining an amount of sulfate-reducing bacteria (SRB) within an oilfield fluid comprising:
amplifying at least one nucleic acid of at least one SRB in the presence of at least one primer to form an amplification product; wherein the amplifying occurs by a PCR amplification method wherein the at least one nucleic acid is extracted from the oilfield fluid prior to amplifying the at least one nucleic acid; wherein the at least one primer comprises a selected from the group consisting of SEQ ID NO.20, SEQ ID NO:21, and mixtures thereof;

hybridizing the amplification product with a probe specific for a fragment of an alpha subunit of an Adenylylsulfate Reductase gene; and detecting a presence of hybridization and a degree of hybridization; wherein the presence of hybridization indicates the presence of the at least one SRB; and wherein the degree of hybridization enumerates the at least one SRB; and determining an amount of SRB in the oilfield fluid.

9. The method of claim 8, wherein the oilfield fluid is selected from the group consisting of oilfield water, a production fluid, a fracturing fluid, a drilling fluid, a completion fluid, a workover fluid, a packer fluid, a gas fluid, a crude oil, and mixtures thereof.

10. The method of claim 8, wherein the probe is detectably labeled.

11. The method of claim 8, wherein the at least one sulfate-reducing bacteria is selected from the group consisting of *Desulfovibrio vulgaris, Desulfovibrio desulfuricans, Desulfovibrio aespoeensis, Thermodesulfobium narugense, Desulfotomaculum carboxydivorans, Desulfotomaculum ruminis, Desulfovibrio africanus, Desulfovibrio hydrothermalis, Desulfovibrio piezophilus, Desulfobacterium corrodens*, Sulfate-reducing bacterium QLNR1, *Desulfobacterium catecholicum, Desulfobulbus marinus, Desulfobulbus, Desulfobulbus propionicus, Desulfocapsa thiozymogenes, Desulfocapsa sulfexigens, Desulforhopalus vacuolatus, Desulforhopalus, Desulfofustis glycolicus* strain, *Desulforhopalus singaporensis, Desulfobacterium, Desulfobacterium zeppelinii* strain, *Desulfobacterium autotrophicum, Desulfobacula phenolica, Desulfobacula toluolica* Tol2, Sulfate-reducing bacterium JHA1, *Desulfospira joergensenii, Desulfobacter, Desulfobacter postgatei, Desulfotignum, Desulfotignum balticum, Desulforegula conservatrix, Desulfocella, Desulfobotulus sapovorans, Desulfofrigus, Desulfonema magnum, Desulfonema limicola, Desulfobacterium indolicum, Desulfosarcina variabilis, Desulfatibacillum, Desulfococcus multivorans, Desulfococcus, Desulfonema ishimotonii Desulfococcus oleovorans* Hxd3, *Desulfococcus niacini, Desulfotomaculum, Desulfotomaculum nigrificans, Desulfotomaculum halophilum, Desulfotomaculum acetoxidans, Desulfotomaculum gibsoniae, Desulfotomaculum sapomandens* strain, *Desulfotomaculum thermosapovorans, Desulfotomaculum geothermicum, Desulfosporosinus meridiei, Delta proteobacterium, Thermodesulforhabdus norvegica, Desulfacinum infernum, Desulfacinum hydrothermale, Desulforhabdus amnigena, Desulforhabdus, Desulfomonile tiedjei, Desulfarculus baarsii, Desulfobacterium anilini, Desulfovibrio profundus* strain, *Desulfomicrobium baculatum, Desulfocaldus hobo, Desulfovibrio, Desulfovibrio piger, Desulfovibrio ferrophilus, Desulfonatronovibrio hydrogenovorans, Desulfovibrio acrylicus, Desulfovibrio salexigens, Desulfovibrio oxyclinae, Desulfonauticus submarinus, Desulfothermus naphthae, Thermodesulfobacterium, Thermodesulfobacterium hveragerdense, Thermodesulfobacterium thermophilum, Thermodesulfatator indicus, Thermodesulfovibrio yellowstonii, Desulfosporosinus orientis, Desulfotomaculum thermobenzoicum, Desulfotomaculum solfataricum, Desulfotomaculum luciae* strain, *Desulfobacca acetoxidans, Desulfovibrio vulgaris, Desulfovibrio desulfuricans, Desulfovibrio alaskensis, Desulfovibrio magneticus, Desulfosporosinus acidiphilus, Desulfotomaculum kuznetsovii, Desulfovibrio sulfodismutans, Desulfonatronum lacustre, Desulfohalobium retbaense, Desulfonauticus autotrophicus, Thermodesulfobacterium commune, Thermodesulfovibrio islandicus, Thermodesulfovibrio, Desulfotomaculum thermoacetoxidans, Desulfotomaculum thermocisternum, Desulfotomaculum australicum, Desulfotomaculum reducens,* and combinations thereof.

12. The method of claim 8, wherein the at least one primer is specific for amplification of at least a fragment of an alpha subunit of APS reductase gene.

13. A PCR amplification method comprising:
amplifying at least one nucleic acid of at least one sulfate-reducing bacteria (SRB) in the presence of at least one primer to form an amplification product; wherein the at least one SRB is extracted from an oilfield fluid prior to amplifying the at least one nucleic acid; wherein the at least one primer comprises a sequence selected from the group consisting of SEQ ID NO.20, SEQ ID NO:21, and mixtures thereof.

14. The method of claim 13, wherein the oilfield fluid is selected from the group consisting of oilfield water, a production fluid, a fracturing fluid, a drilling fluid, a completion fluid, a workover fluid, a packer fluid, a gas fluid, a crude oil, and mixtures thereof.

15. The method of claim 13, wherein the at least one sulfate-reducing bacteria is selected from the group consisting of *Desulfovibrio vulgaris, Desulfovibrio desulfuricans, Desulfovibrio aespoeensis, Thermodesulfobium narugense, Desulfotomaculum carboxydivorans, Desulfotomaculum ruminis, Desulfovibrio africanus, Desulfovibrio hydrothermalis, Desulfovibrio piezophilus, Desulfobacterium corrodens*, Sulfate-reducing bacterium QLNR1, *Desulfobacterium catecholicum, Desulfobulbus marinus, Desulfobulbus, Desulfobulbus propionicus, Desulfocapsa thiozymogenes, Desulfocapsa sulfexigens, Desulforhopalus vacuolatus,*

*Desulforhopalus, Desulfofustis glycolicus* strain, *Desulforhopalus singaporensis, Desulfobacterium, Desulfobacterium zeppelinii* strain, *Desulfobacterium autotrophicum, Desulfobacula phenolica, Desulfobacula toluolica* Tol2, Sulfate-reducing bacterium JHA1, *Desulfospira joergensenii, Desulfobacter, Desulfobacter postgatei, Desulfotignum, Desulfotignum balticum, Desuforegula conservatrix, Desulfocella, Desulfobotulus sapovorans, Desulfofrigus, Desulfonema magnum, Desulfonema limicola, Desulfobacterium indolicum, Desulfosarcina variabilis, Desulfatibacillum, Desulfococcus multivorans, Desulfococcus, Desulfonema ishimotonii Desulfococcus oleovorans* Hxd3, *Desulfococcus niacini, Desulfotomaculum, Desulfotomaculum nigrificans, Desulfotomaculum halophilum, Desulfotomaculum acetoxidans, Desulfotomaculum gibsoniae, Desulfotomaculum sapomandens* strain, *Desulfotomaculum thermosapovorans, Desulfotomaculum geothermicum, Desulfosporosinus meridiei, Delta proteobacterium, Thermodesulforhabdus norvegica, Desulfacinum infernum, Desulfacinum hydrothermale, Desulforhabdus amnigena, Desulforhabdus, Desulfomonile tiedjei, Desulfarculus baarsii,* Sulfate-reducing bacterium, Sulfate-reducing bacterium, Sulfate-reducing bacterium, *Desulfobacterium anilini, Desulfovibrio profundus* strain, *Desulfomicrobium baculatum, Desulfocaldus hobo, Desulfovibrio, Desulfovibrio piger, Desulfovibrio ferrophilus, Desulfonatronovibrio hydrogenovorans, Desulfovibrio acrylicus, Desulfovibrio salexigens, Desulfovibrio oxyclinae, Desulfonauticus submarinus, Desulfothermus naphthae, Thermodesulfobacterium, Thermodesulfobacterium hveragerdense, Thermodesulfobacterium thermophilum, Thermodesulfatator indicus, Thermodesulfovibrio yellowstonii, Desulfosporosinus orientis, Desulfotomaculum thermobenzoicum, Desulfotomaculum solfataricum, Desulfotomaculum luciae* strain, *Desulfobacca acetoxidans, Desulfovibrio vulgaris, Desulfovibrio desulfuricans, Desulfovibrio alaskensis, Desulfovibrio magneticus, Desulfosporosinus acidiphilus, Desulfotomaculum kuznetsovii, Desulfovibrio sulfodismutans, Desulfonatronum lacustre, Desulfohalobium retbaense, Desulfonauticus autotrophicus, Thermodesulfobacterium commune, Thermodesulfovibrio islandicus, Thermodesulfovibrio, Desulfotomaculum thermoacetoxidans, Desulfotomaculum thermocisternum, Desulfotomaculum australicum, Desulfotomaculum reducens,* and combinations thereof.

\* \* \* \* \*

SEQUENCE LISTING

```
<160> NUMBER OF SEQ ID NOS: 21

<210> SEQ ID NO 1
<211> LENGTH: 21
<212> TYPE: DNA
<213> ORGANISM: Artificial Sequence
<220> FEATURE:
<223> OTHER INFORMATION: Sulfate Reducing Bacteria
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 1
ccngtncgya ccggtaaatg g                                           21

<210> SEQ ID NO 2
<211> LENGTH: 18
<212> TYPE: DNA
<213> ORGANISM: Artificial Sequence
<220> FEATURE:
<223> OTHER INFORMATION: Sulfate Reducing Bacteria
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 2
ccngtnggcg cntggttc                                               18

<210> SEQ ID NO 3
<211> LENGTH: 17
<212> TYPE: DNA
<213> ORGANISM: Artificial Sequence
<220> FEATURE:
<223> OTHER INFORMATION: Sulfate Reducing Bacteria
<220> FEATURE:
<221> NAME/KEY: misc_feature
<222> LOCATION: (12)..(12)
<223> OTHER INFORMATION: n is a, c, g, or t

<400> SEQUENCE: 3
```

```
gagaacttgt gnccgga                                                  17
```

<210> SEQ ID NO 4
<211> LENGTH: 15
<212> TYPE: DNA
<213> ORGANISM: Artificial Sequence
<220> FEATURE:
<223> OTHER INFORMATION: Sulfate Reducing Bacteria

<400> SEQUENCE: 4

```
cayacccagg gytgg                                                    15
```

<210> SEQ ID NO 5
<211> LENGTH: 14
<212> TYPE: DNA
<213> ORGANISM: Artificial Sequence
<220> FEATURE:
<223> OTHER INFORMATION: Sulfate Reducing Bacteria

<400> SEQUENCE: 5

```
cacacbaagg dtgg                                                     14
```

<210> SEQ ID NO 6
<211> LENGTH: 15
<212> TYPE: DNA
<213> ORGANISM: Artificial Sequence
<220> FEATURE:
<223> OTHER INFORMATION: Sulfate Reducing Bacteria

<400> SEQUENCE: 6

```
cayacbcaag gctgg                                                    15
```

<210> SEQ ID NO 7
<211> LENGTH: 15
<212> TYPE: DNA
<213> ORGANISM: Artificial Sequence
<220> FEATURE:
<223> OTHER INFORMATION: Sulfate Reducing Bacteria

<400> SEQUENCE: 7

```
catacdcagg ghtgg                                                    15
```

<210> SEQ ID NO 8
<211> LENGTH: 15
<212> TYPE: DNA
<213> ORGANISM: Artificial Sequence
<220> FEATURE:
<223> OTHER INFORMATION: Sulfate Reducing Bacteria

<400> SEQUENCE: 8

```
cacacdcagg grtgg                                                    15
```

<210> SEQ ID NO 9
<211> LENGTH: 15
<212> TYPE: DNA
<213> ORGANISM: Artificial Sequence
<220> FEATURE:
<223> OTHER INFORMATION: Sulfate Reducing Bacteria

<400> SEQUENCE: 9

```
cacacdcagg gytgg                                                    15
```

<210> SEQ ID NO 10
<211> LENGTH: 15
<212> TYPE: DNA
<213> ORGANISM: Artificial Sequence

```
<220> FEATURE:
<223> OTHER INFORMATION: Sulfate Reducing Bacteria
<220> FEATURE:
<221> NAME/KEY: misc_feature
<222> LOCATION: (12)..(12)
<223> OTHER INFORMATION: n is a, c, g, or t

<400> SEQUENCE: 10
catacccagg gntay                                                   15

<210> SEQ ID NO 11
<211> LENGTH: 15
<212> TYPE: DNA
<213> ORGANISM: Artificial Sequence
<220> FEATURE:
<223> OTHER INFORMATION: Sulfate Reducing Bacteria

<400> SEQUENCE: 11
catacwcagg ghtat                                                   15

<210> SEQ ID NO 12
<211> LENGTH: 21
<212> TYPE: DNA
<213> ORGANISM: Artificial Sequence
<220> FEATURE:
<223> OTHER INFORMATION: Sulfate Reducing Bacteria
<220> FEATURE:
<221> NAME/KEY: misc_feature
<222> LOCATION: (7)..(7)
<223> OTHER INFORMATION: n is a, c, g, or t

<400> SEQUENCE: 12
ccatacnggr taccakgcrc g                                             21

<210> SEQ ID NO 13
<211> LENGTH: 19
<212> TYPE: DNA
<213> ORGANISM: Artificial Sequence
<220> FEATURE:
<223> OTHER INFORMATION: Sulfate Reducing Bacteria
<220> FEATURE:
<221> NAME/KEY: misc_feature
<222> LOCATION: (14)..(14)
<223> OTHER INFORMATION: n is a, c, g, or t

<400> SEQUENCE: 13
ggaagtcttc ccangcttc                                               19

<210> SEQ ID NO 14
<211> LENGTH: 21
<212> TYPE: DNA
<213> ORGANISM: Artificial Sequence
<220> FEATURE:
<223> OTHER INFORMATION: Sulfate Reducing Bacteria

<400> SEQUENCE: 14
tgggaagabt tcctvgacat g                                            21

<210> SEQ ID NO 15
<211> LENGTH: 17
<212> TYPE: DNA
<213> ORGANISM: Artificial Sequence
<220> FEATURE:
<223> OTHER INFORMATION: Sulfate Reducing Bacteria

<400> SEQUENCE: 15
gtgtarcagt trccrca                                                 17
```

```
<210> SEQ ID NO 16
<211> LENGTH: 26
<212> TYPE: DNA
<213> ORGANISM: Artificial Sequence
<220> FEATURE:
<223> OTHER INFORMATION: Sulfate Reducing Bacteria

<400> SEQUENCE: 16
cagatcatga tcaayggtga rtcyta                                          26

<210> SEQ ID NO 17
<211> LENGTH: 19
<212> TYPE: DNA
<213> ORGANISM: Artificial Sequence
<220> FEATURE:
<223> OTHER INFORMATION: Sulfate Reducing Bacteria
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 17
cgaagactac tgngnvacc                                                  19

<210> SEQ ID NO 18
<211> LENGTH: 21
<212> TYPE: DNA
<213> ORGANISM: Artificial Sequence
<220> FEATURE:
<223> OTHER INFORMATION: Sulfate Reducing Bacteria
<220> FEATURE:
<221> NAME/KEY: misc_feature
<222> LOCATION: (14)..(14)
<223> OTHER INFORMATION: n is a, c, g, or t

<400> SEQUENCE: 18
cgcccacdcc gtcngcvcag g                                               21

<210> SEQ ID NO 19
<211> LENGTH: 15
<212> TYPE: DNA
<213> ORGANISM: Artificial Sequence
<220> FEATURE:
<223> OTHER INFORMATION: Sulfate Reducing Bacteria

<400> SEQUENCE: 19
tsaacatgtg cggcg                                                      15

<210> SEQ ID NO 20
<211> LENGTH: 29
<212> TYPE: DNA
<213> ORGANISM: Unknown
<220> FEATURE:
<223> OTHER INFORMATION: Sulfate Reducing Bacteria
<220> FEATURE:
<221> NAME/KEY: misc_feature
<222> LOCATION: (24)..(24)
<223> OTHER INFORMATION: n is a, c, g, or t

<400> SEQUENCE: 20
aataaatcat aagagaactt gtgnccgga                                       29

<210> SEQ ID NO 21
<211> LENGTH: 33
```

```
<212> TYPE: DNA
<213> ORGANISM: Unknown
<220> FEATURE:
<223> OTHER INFORMATION: Sulfate Reducing Bacteria

<400> SEQUENCE: 21 ataaatcat aatgggaaga bttcctvgac atg                              33
```